(12) United States Patent
Reithinger

(10) Patent No.: US 7,796,271 B2
(45) Date of Patent: Sep. 14, 2010

(54) EAR CANAL HOLOGRAM FOR HEARING APPARATUSES

(75) Inventor: Jürgen Reithinger, Neunkirchen am Brand (DE)

(73) Assignee: Siemens Audiologisch Technik GmbH, Erlangen (DE)

(*) Notice: Subject to any disclaimer, the term of this patent is extended or adjusted under 35 U.S.C. 154(b) by 39 days.

(21) Appl. No.: 11/998,395

(22) Filed: Nov. 29, 2007

(65) Prior Publication Data

US 2008/0130930 A1 Jun. 5, 2008

Related U.S. Application Data

(60) Provisional application No. 60/872,762, filed on Dec. 4, 2006.

(51) Int. Cl.
*G01B 9/021* (2006.01)
(52) U.S. Cl. ..................................... 356/457
(58) Field of Classification Search ................. 356/457, 356/458, 511, 512; 381/329, 328; 264/238, 264/222
See application file for complete search history.

(56) References Cited

U.S. PATENT DOCUMENTS

| | | | |
|---|---|---|---|
| 4,611,288 A | | 9/1986 | Duret et al. |
| 4,643,514 A | * | 2/1987 | Raviv et al. ................. 600/108 |
| 5,014,709 A | * | 5/1991 | Bjelkhagen et al. ......... 600/431 |
| 6,798,569 B2 | | 9/2004 | Bewersdorf et al. |
| 7,127,109 B1 | * | 10/2006 | Kim ........................... 382/210 |
| 7,486,406 B2 | * | 2/2009 | Kim ........................... 356/497 |
| 2002/0105723 A1 | | 8/2002 | Bewersdorf et al. |
| 2004/0138590 A1 | * | 7/2004 | Jensen et al. ................. 600/587 |
| 2005/0078361 A1 | | 4/2005 | Bewersdorf et al. |
| 2006/0074509 A1 | | 4/2006 | Di Fabrizio et al. |
| 2006/0276709 A1 | | 12/2006 | Khamene et al. |
| 2007/0142707 A1 | * | 6/2007 | Wiklof et al. ................ 600/118 |
| 2009/0128825 A1 | * | 5/2009 | Akcakir ....................... 356/457 |

FOREIGN PATENT DOCUMENTS

| | | |
|---|---|---|
| EP | 1223450 A2 | 7/2002 |
| WO | WO 03105685 A2 | 12/2003 |

OTHER PUBLICATIONS

Klattenhoff et al., Miniaturized sensor head for distal holographic endoscopy, 2003, SPIE, vol. 5145, 137-145.*
Kolenovic et el., Miniaturized digital holography sensor for distal three-dimensional endoscopy, 2003, Optical Society of America, vol. 42, 5167-5172.*

* cited by examiner

*Primary Examiner*—Tarifur Chowdhury
*Assistant Examiner*—Jonathan M Hansen

(57) ABSTRACT

The aim is to be able to determine the spatial structure of an ear canal in a simple and reliable fashion. To this end, it is proposed to produce a hologram of the ear canal, by inserting a holography unit at least partially into the ear canal. The data for the shape of a housing shell or an otoplastic can then be obtained from the resulting hologram for automatic manufacturing methods.

17 Claims, 3 Drawing Sheets

EAR CANAL HOLOGRAM FOR HEARING APPARATUSES

CROSS REFERENCE TO RELATED APPLICATIONS

The present application claims the benefit of the provisional patent application filed on Dec. 4, 2006, and assigned application No. 60/872,762, which is incorporated by reference herein in its entirety.

FIELD OF THE INVENTION

The present invention relates to a recording apparatus for recording the spatial structure of at least one part of an ear canal or ear impression. The present invention also relates to a facility for producing a housing shell or an otoplastic for a hearing apparatus as well as a corresponding recording method and a production method. Hearing apparatus is understood here to mean in particular a hearing device, but also a headset, headphones or suchlike.

Hearing devices are wearable hearing apparatuses used to assist the hard-of-hearing. To meet the numerous individual requirements, different designs of hearing device are provided, such as behind-the ear (BTE) hearing devices, in-the-ear (ITE) hearing devices and concha hearing devices. The typical configurations of hearing device are worn on the outer ear or in the auditory canal. Above and beyond these designs however bone conduction hearing aids, implantable or vibro-tactile hearing aids are also available on the market. In such hearing aids the damaged hearing is stimulated either mechanically or electrically.

Hearing devices principally have as their main components an input converter, an amplifier and an output converter. The input converter is as a rule a sound receiver, e.g. a microphone, and/or an electromagnetic receiver, e.g. an induction coil. The output converter is mostly implemented as an electroacoustic converter, e.g. a miniature loudspeaker, or as an electromechanical converter, e.g. bone conduction earpiece. The amplifier is usually integrated into a signal processing unit. This basic structure is shown in FIG. 1 using a behind-the ear hearing device as an example. One or more microphones 2 for recording the sound from the surroundings are built into a hearing device housing 1 worn behind the ear. A signal processing unit 3, which is also integrated into the hearing device housing 1, processes the microphone signals and amplifies them. The output signal of the signal processing unit 3 is transmitted to a loudspeaker or earpiece 4 which outputs an acoustic signal. The sound is transmitted, if necessary via a sound tube which is fixed with an otoplastic in the auditory canal, to the hearing device wearer's eardrum. The power is supplied to the hearing device and especially to the signal processing unit 3 by a battery 5 also integrated into the hearing device housing 1.

Methods are required to produce ITE hearing devices, with which the shape of the auditory canal can be transferred to the housing shell of an ITE hearing device in as precise a manner as possible. An ear impression of an auditory canal is usually taken in order to produce the shape for a housing shell therefrom. Ear impressions of this type have been read into PC systems by means of scanning for some time, in order then to be further processed digitally. These scanners mostly use the triangulation method for measuring the 3D data of the objects. To this end, a light source (projector) is used, which projects a pattern. This pattern is recorded again by a camera, which is disposed at an angle from the projector. The spatial depth structure can be calculated herefrom.

Methods are also known, in which the auditory canal is directly scanned, without requiring an ear impression. These scanners, like those used to record an ear impression, are relatively expensive and are almost exclusively based on tri-angulation measurement methods, which necessitate precise optical systems and also require a complex system adjustment.

The publication WO 02/071794 A1 discloses such a method for modeling individual ear pieces. In this process, a 3D scanner is used, in order to obtain a virtual model of the ear canal. The ear piece is then manufactured on the basis of the 3D model.

A so-called Rapid Prototyping and Production is suited to producing housing shells or otoplastics for hearing apparatuses. Different methods are described for this in the publication DE 696 34 921 P2 for instance. In particular, stereolithographic methods are used in this context, in order to produce plastic hearing device shells or otoplastics.

The publication WO 03/105685 A2 discloses a device for determining the structure of the auditory canal, which is based on the conoscopic principle. The beam reflected by an object to be calibrated is separated in a conoscopic module into an ordinary and special part. An interference pattern can herewith be obtained, from which the distance of the object point from the sensor can be determined. In the case of the device shown, a moveable mirror, which deflects the illumination and reflected object beam, is introduced into the ear canal.

A microscope is also known from the publication EP 1 223 450 A2. A reference object for the calibration, adjustment and setting of the microscope is provided in order to operate the microscope.

SUMMARY OF THE INVENTION

The object of the present invention consists in obtaining information relating to the spatial structure of at least one part of an ear canal in a simple and reliable fashion.

This object is achieved in accordance with the invention by a recording apparatus for recording the spatial structure of at least one part of an ear canal or ear impression using a holography unit, which comprises a light source and by means of which a hologram of the ear canal can be adjusted, by introducing the holography unit at least partially into the ear canal, with the holography unit comprising a semitransparent disk for separating the light beam from the light source into an illumination beam and a reference beam and comprising a recording sensor for recording an object beam, which is produced by reflection of the illumination beam onto the part of the ear canal, together with the reference beam.

Accordingly, provision is also made for a corresponding method for recording the spatial structure of at least one part of an ear canal or ear impression by producing a hologram of the ear canal, by introducing a holography unit at least partially into the ear canal, with a light beam of a light source being divided into an illumination beam and a reference beam and by an object beam, which is produced by reflecting the illumination beam onto the part of the ear canal, being recorded together with the reference beam as a hologram in the ear canal, by means of a recording sensor.

Provision is also made in accordance with the invention for a facility for producing a housing shell or an otoplastic for a hearing apparatus with an afore-illustrated recording apparatus and a molding unit (a Rapid Shell Modeling unit or RSM unit) for molding the housing shell or the otoplastic from the hologram of the ear canal obtained by means of the recording apparatus.

Provision is likewise made for a corresponding method for producing a housing shell or an otoplastic for a hearing apparatus by recording the spatial structure of at least one part of an ear canal and molding the housing shell or the otoplastic from the obtained hologram of the ear canal.

The afore-mentioned recording apparatus preferably comprises a guide facility, with which the holography unit in the ear canal can be pivoted, rotated and moved along the ear canal. The curved ear canal can thus be recorded in a desired fashion.

It is also favorable if a number of individual holograms can be recorded by the holography unit and combined to form the hologram of the ear canal, i.e. overall hologram. The ear canal and/or the ear impression can thus be recorded from different perspectives, so that a very precise hologram of the ear canal can be produced.

Furthermore, the holography unit can be suited to producing a digital hologram of the ear canal. The digital data can then be used directly for the production of the housing shell and/or the otoplastic of the hearing apparatus.

As a recording sensor, the holography unit can comprise in particular a CCD chip or a CMOS chip. By this means, recording raw data can already be obtained in digital form.

It is also advantageous if a reference object is also recorded when the ear canal is recorded for the hologram. This then allows the recording to be calibrated so that it can be used for the actual measurements and/or production of the housing shell or otoplastic. In particular, an automatic calibration can be carried out on the basis of the reference object. Regular calibrations can thus be carried out without any great effort, so that a high-quality hologram can always be ensured.

BRIEF DESCRIPTION OF THE DRAWINGS

The present invention is described in more detail with reference to the appended drawings, in which.

DETAILED DESCRIPTION OF THE INVENTION

The exemplary embodiment illustrated in more detail below represents a preferred embodiment of the present invention. The principle behind holography is however first explained in brief on the basis of FIG. 2, in order to gain a better understanding of the structure of the inventive device in accordance with FIG. 3.

Figure 1:
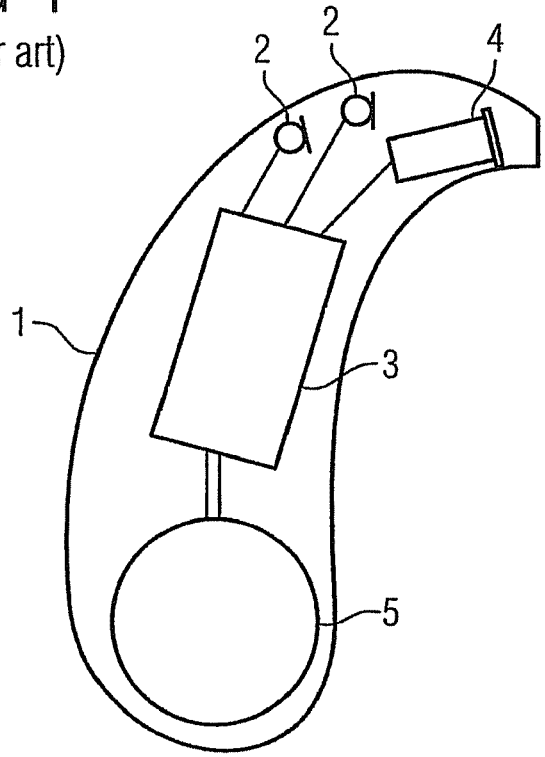
FIG. 1 shows the basic design of a hearing device according to the prior art.
Figure 2:
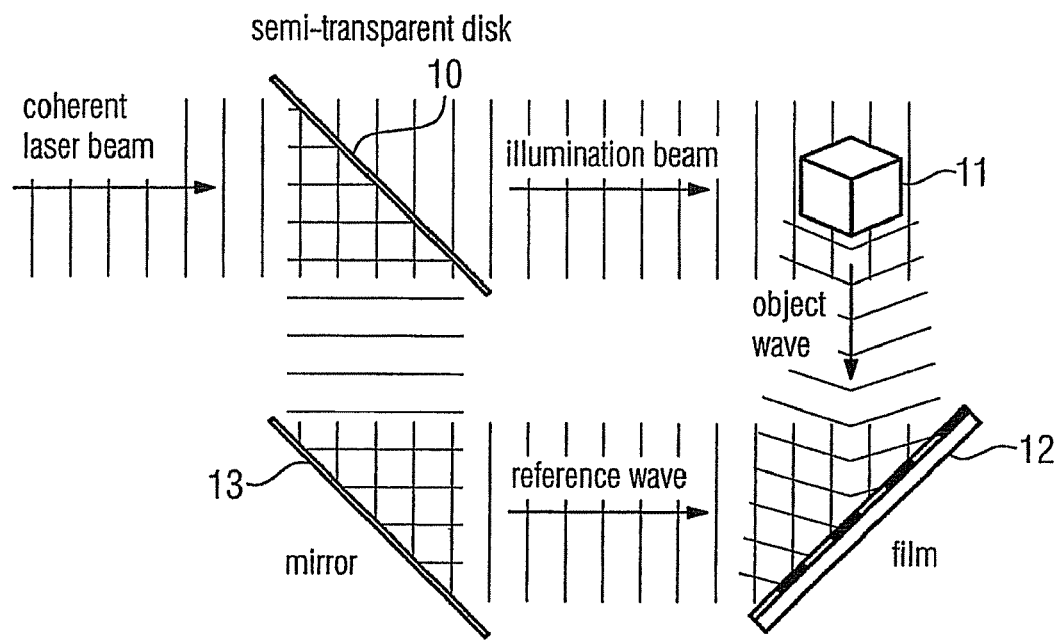
FIG. 2 shows a basic representation for obtaining a hologram.

In accordance with FIG. 2, a coherent laser beam is sent to a semi-transparent disk 10 in order to obtain a hologram. One part of the laser beam penetrates the semi-transparent disk and forms an illumination beam, which strikes the object 11, here the ear canal or the ear impression. One part of the illumination beam is reflected onto the object 11 and forms an object wave, which hits a film 12. At the same time, one part of the coherent laser beam is deflected for this purpose by the semi-transparent disk onto a mirror 13 and from there further onto the film 12 as a reference source. The object wave overlaps the reference wave on the film 12, thereby resulting in the hologram. To be able to observe the hologram, the illuminated and developed film is in turn radiated with a coherent laser beam.

Figure 3:
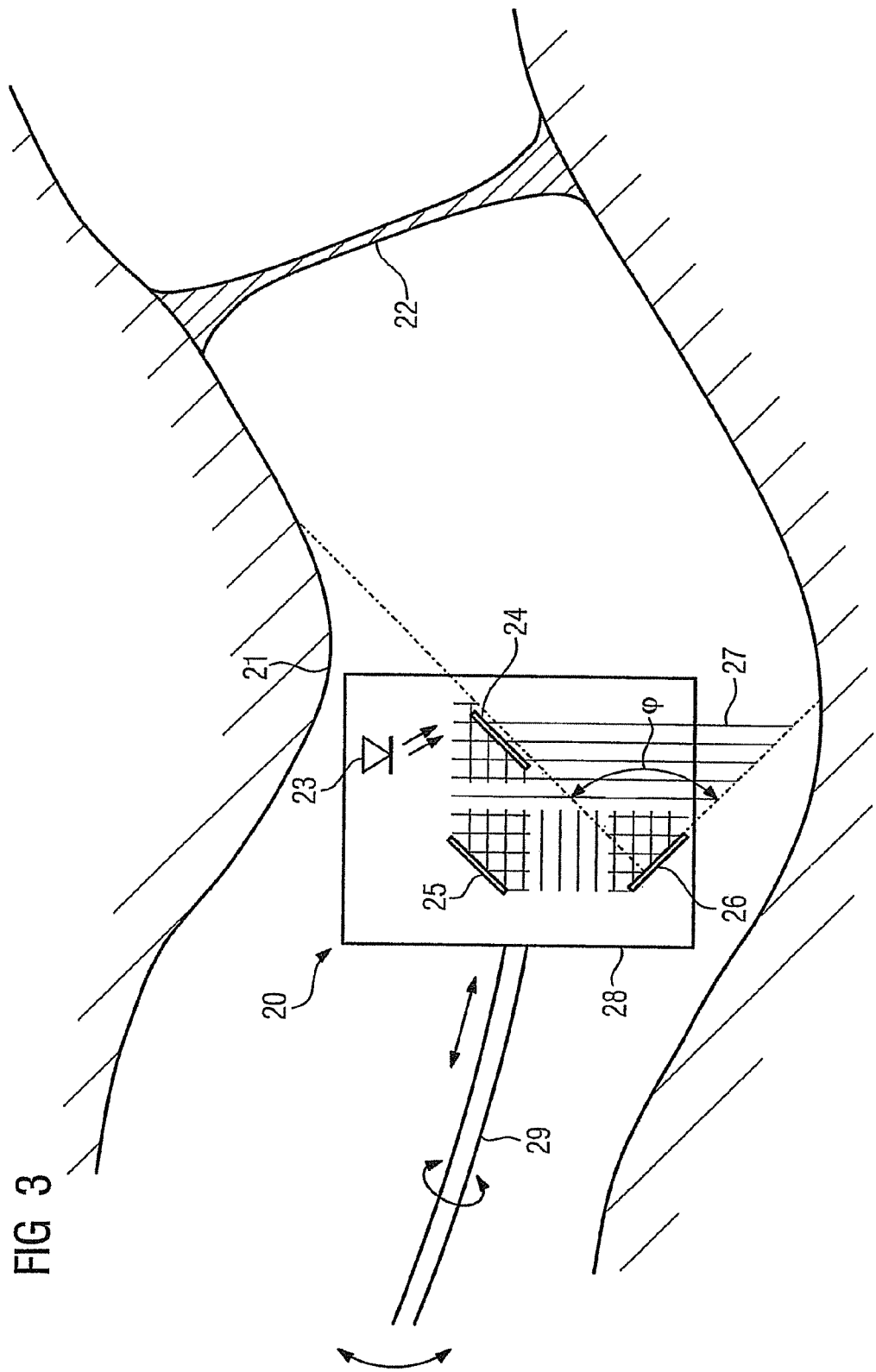
FIG. 3 shows a schematic representation of an inventive hologram recording device in an ear canal.
Figure 4:
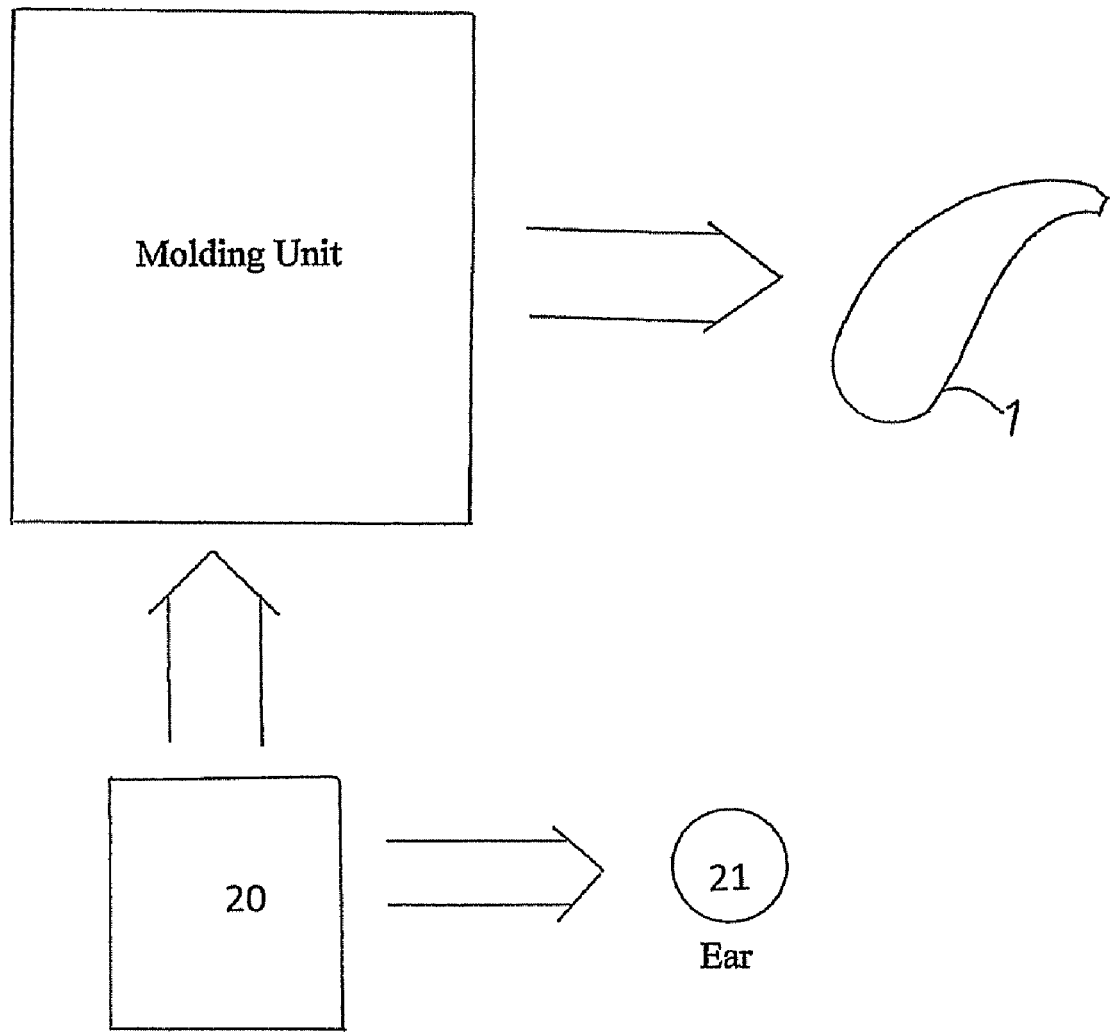
FIG. 4 shows a schematic representation of production of an ear piece utilizing the recording device and molding unit.

According to the present invention, this hologram recording technique is now used to record and/or to calibrate the spatial structure of an ear canal. To this end, the hologram recording device 20 illustrated schematically in FIG. 3 is used. According to the representation in FIG. 2, this recording device 20 is located in an ear canal 21, which is delimited on its interior by an eardrum 22. The ear canal 21 is curved, so that it is not easily visible in its entirety from the outside.

The recording device 20 essentially exhibits the structure, which was illustrated in conjunction with FIG. 2. In the case of the concrete design in FIG. 3, a laser diode 23 is used as a light source for the coherent laser light. One part of the light is deflected to a recording sensor 26 by way of a semi-transparent disk 24 and a mirror 25. Another part of the laser light is guided through the semi-transparent disk and radiated into the ear canal 21. For overview purposes, the optical elements for radiating the light into the ear canal are not shown in FIG. 3. This only shows the wave front 27, which is reflected back by the ear canal 21, and reaches the recording sensor 26. The recording sensor 26, e.g. a CCD sensor, is used instead of a photo disk and/or film 12, so that practically any number of recordings can be recorded without replacing a film or disk. The data can also be digitally obtained directly from the recording sensor and thus processed in a distortion-free fashion.

The geometric arrangement and the optical characteristics of the components of the recording device 20 determine the maximum recording angle $\phi$. As in the field this angle $\phi$ is not permitted to be arbitrarily large, it is generally necessary to record a number of individual holograms from different positions of the recording device 20 and to combine these using a computer to form an overall hologram. To this end, it is necessary for the recording device to able to be positioned and aligned differently in the ear canal. The size of the recording device 20 may subsequently not exceed a specific maximum size, so that a certain moveability remains ensured in the ear canal.

In order to move the recording device 20, a guide element 29 is fastened to its housing 28. This guide element 29 allows the recording device 20 to be tilted, rotated and moved along the ear canal 21 in accordance with the arrows illustrated in FIG. 3. The guide element may be a flexible rod for instance.

The hologram recording system can essentially be constructed within smaller dimensions than a conventional 3D scanner, which is based on the triangulation principle. This 3D scanner namely requires a projector and a camera, which have to be aligned exactly at a specific angle to one another. In contrast, the hologram recording system only requires one laser (laser diode) and a semi-transparent mirror aligned thereto, a further deflection mirror as well as a recording sensor likewise aligned thereto. The hologram recording system can be constructed within significantly smaller dimensions than the 3D scanner. The hologram sensor (CCD chip) does not require a front lens, since it does not record a mapping of an image, but instead interference patterns on its surface. Neither do any depth of field problems arise. All that happens is that resolution is marginally reduced at the edge. This can however be balanced by making a number of recordings from different positions.

The measurement accuracy of the hologram recording system depends on the position of the CCD chip 26 in respect of the mirrors 24, 25 and the laser 23. To achieve the desired measurement accuracy, a corresponding calibration is necessary. This can essentially occur by means of a once-off calibration. It can however also be automatically calibrated at predetermined time intervals or with each measurement. To this end, a measurement reference object is also recorded during the hologram recording. This measurement reference object exhibits a known size and shape, such as for instance a small 3D star. The entire remaining hologram can be calibrated and an exact 3D image reconstructed in the PC with the aid of said hologram. To this end, the hologram is converted into a scatter plot in a known manner. Provided the PC's computing power permits, a fully automatic calibration is even possible during the measurement with the aid of the reference object.

On the basis of the 3D image obtained in the PC, which is present without any significant shadings as a result of the different recording positions, hairs in the auditory canal can then even be recognized and removed from the image and/or the data model for the housing production since the complete 3D image of the ear canal has to be present without any significant shadings.

The invention claimed is:

1. A recording apparatus for recording a spatial structure of a portion of an ear canal of a person, comprising:
   a holography unit that inserts into the ear canal;
   a light source arranged on the holography unit that emits a light beam;
   a semi-transparent disk arranged on the holography unit that divides the light beam into an illumination beam and a reference beam; and
   a mirror arranged on the holography unit arranged to redirect the reference beam coming from the semi-transparent disk directly onto a digital recording sensor,
   wherein the digital recording sensor is arranged on the holography unit and directly records a hologram of the ear canal by recording an interference pattern produced via the reference beam redirected by the mirror and an object beam, where the object beam is produced by reflecting the illumination beam onto the portion of the ear canal.

2. The recording apparatus as claimed in claim 1, further comprising a guide unit that pivots, rotates, and moves the holography unit in the ear canal.

3. The recording apparatus as claimed in claim 1, wherein a plurality of individual holograms of the ear canal are recorded by the holography unit and are combined to generate the hologram of the ear canal.

4. The recording apparatus as claimed in claim 1, wherein the hologram of the ear canal is a digital hologram.

5. The recording apparatus as claimed in claim 1, wherein the digital recording sensor is a CCD chip.

6. The recording apparatus as claimed in claim 1, wherein the recording apparatus records an ear impression of the person.

7. The recording apparatus as claimed in claim 1, wherein the holography unit is at least partially inserted into the ear canal.

8. The recording apparatus as claimed in claim 1, wherein a reference object with a known size and shape is recorded by the holography unit.

9. The recording apparatus as claimed in claim 8, wherein the holography unit is calibrated based on the reference object.

10. An apparatus for producing a housing shell of a hearing apparatus, comprising:
    a holography unit comprising a holography unit housing, wherein the holography unit inserts into an ear canal of a user of the hearing apparatus;
    a light source arranged on the holography unit that emits a light beam;
    a semi-transparent disk arranged on the holography unit that divides the light beam into an illumination beam and a reference beam;
    a redirecting mirror arranged on the holography unit;
    a digital recording sensor arranged on the holography unit that directly records a hologram of the ear canal by recording an interference pattern produced via the reference beam, where the reference beam is redirected by the redirecting mirror onto the digital recording sensor, and an object beam, where the object beam is produced by reflecting the illumination beam onto a portion of the ear canal; and
    an RSM molding unit that molds the housing shell from the hologram of the ear canal,
    wherein the holography unit, the light source, the semi-transparent disk, the redirecting mirror, and the digital recording sensor are all contained within the holography unit housing.

11. The apparatus as claimed in claim 10, wherein the RSM molding unit molds an otoplastic of the hearing apparatus from the hologram of the ear canal.

12. A method for recording a spatial structure of a portion of an ear canal of a person, comprising
    inserting a holography unit into the ear canal, the holography unit comprising a light source and a recording sensor contained within a holography unit housing;
    dividing a light beam of the light source into an illumination beam and a reference beam using a semi-transparent disk contained within the holography unit housing;
    reflecting the reference beam onto a recording surface of a digital image recording sensor contained within the holography unit housing a reflecting mirror also contained within the holography unit housing, wherein the reflecting mirror reflects the reference beam directly onto the digital image recording sensor;
    reflecting the illumination beam onto the portion of the ear canal to generate an object beam; and
    recording an interference pattern produced on the recording surface of a digital image recording sensor where the interference pattern is produced by the object beam and the reflected reference beam to record a hologram of the ear canal.

13. The method as claimed in claim 12, wherein the hologram of the ear canal is a digital hologram.

14. The method as claimed in claim 12, wherein a plurality of individual holograms of the ear canal are recorded by the holography unit and are combined to generate the hologram of the ear canal.

15. The method as claimed in claim 12, wherein a reference object with a known size and shape is recorded by the holography unit.

16. The method as claimed in claim 15, wherein the holography unit is calibrated based on the reference object.

17. The method as claimed in claim 16, wherein the calibration is performed automatically.

* * * * *